United States Patent [19]

Yamauchi

[11] Patent Number: 4,546,254
[45] Date of Patent: Oct. 8, 1985

[54] CHARGED PARTICLE ENERGY ANALYZER

[75] Inventor: Hiroshi Yamauchi, Uji, Japan

[73] Assignee: Shimadzu Corporation, Kyoto, Japan

[21] Appl. No.: 478,348

[22] Filed: Mar. 24, 1983

[51] Int. Cl.⁴ ............................................. H01J 49/48
[52] U.S. Cl. ..................................... 250/305; 250/310
[58] Field of Search ......................... 250/305, 310, 306

[56] References Cited

U.S. PATENT DOCUMENTS 3,749,926  7/1973  Lee ....................................... 250/305
3,790,781  2/1974  Horl et al. ............................ 250/310

Primary Examiner—Alfred E. Smith
Assistant Examiner—Jack I. Berman
Attorney, Agent, or Firm—Birch, Stewart, Kolasch & Birch

[57] ABSTRACT

A charged particle energy analyzer comprises a source for generating radiation to be incident on a sample so as to emit charged particles from the sample, a low energy pass reflection filter for selectively reflecting the charged particles having energy lower than a first value, a high energy pass transmission filter for selectively transmitting the charged particles having energy higher than a second value. The low energy pass reflecting filter comprises a reflector and a first grid. The reflector is a spheroid mirror having two complex focuses, disposed in a symmetrical manner, at which the sample and a detector are disposed. The detector detects the selected charged particles.

9 Claims, 4 Drawing Figures

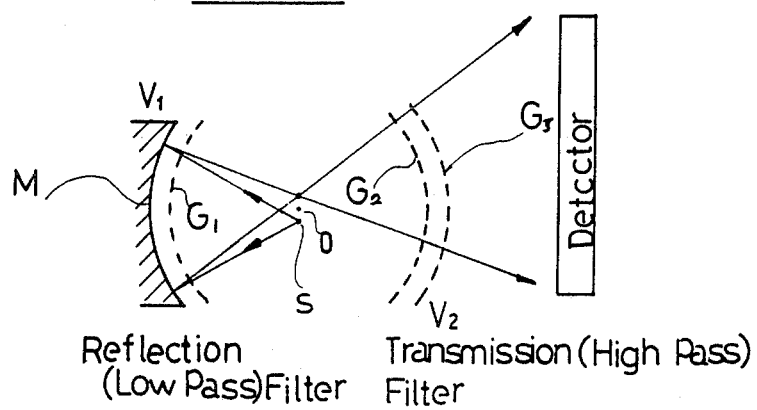
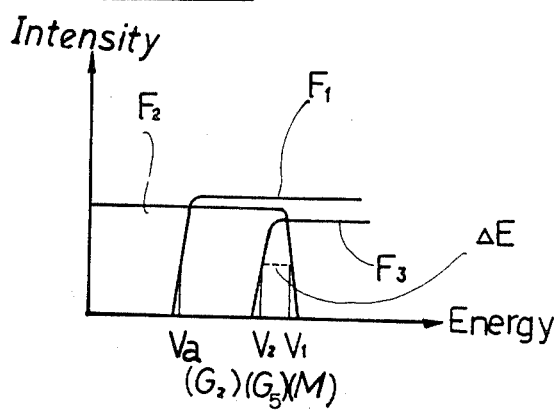
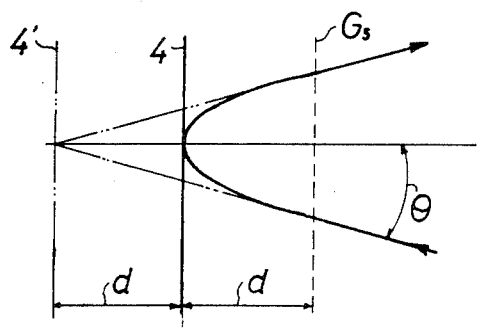

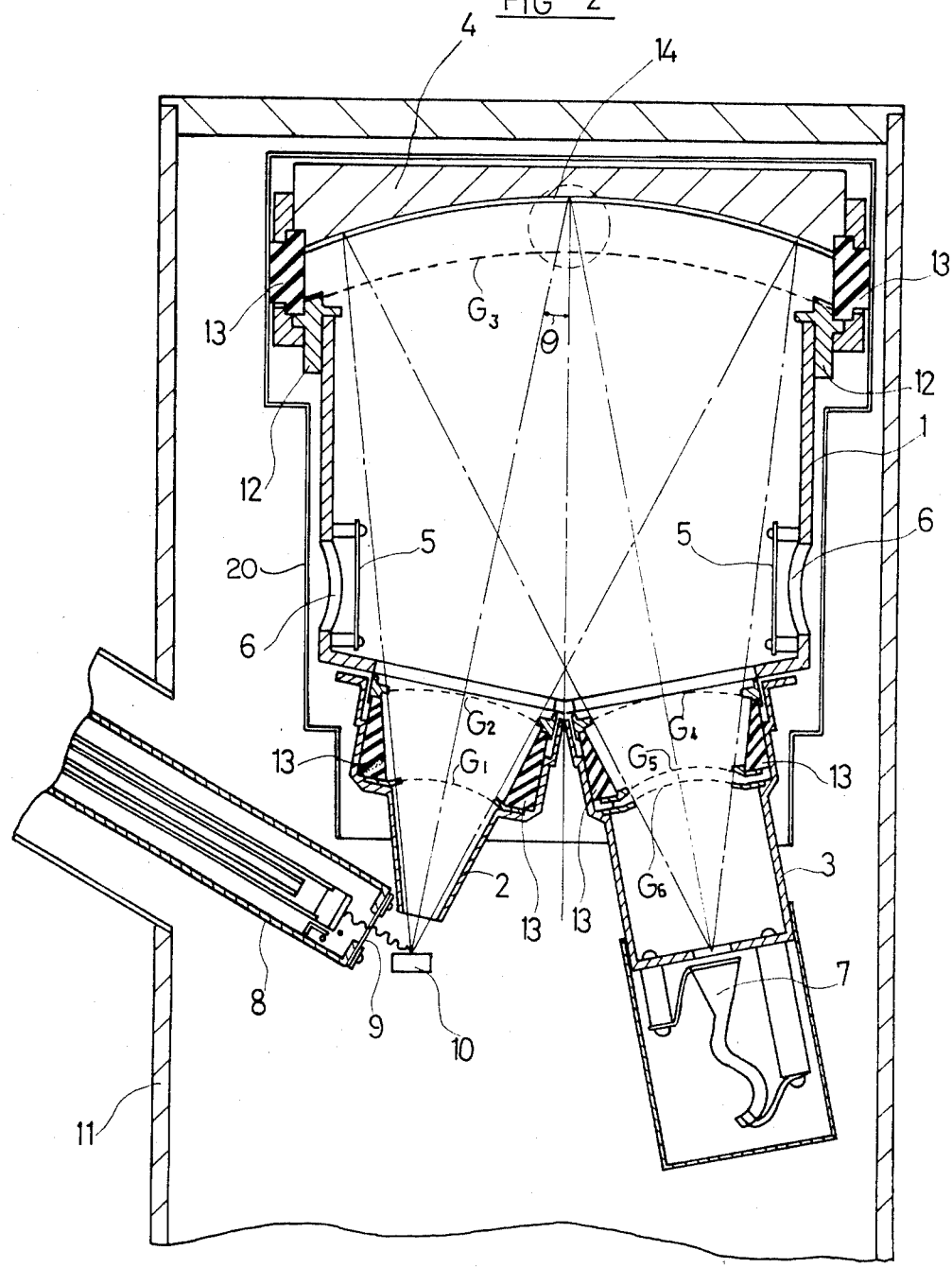

CHARGED PARTICLE ENERGY ANALYZER

BACKGROUND OF THE INVENTION

The present invention relates to a charged particle energy analyzer for such things as electron spectroscopy and ion spectroscopy, and, more particularly, to an energy analyzer of the type in which a low energy pass reflection filter and a high energy pass transmission filter are combined to measure the energy of charged particles generated from a sample.

FIG. 1 shows one of the conventional combinations of a low energy pass reflection filter and a high energy pass transmission filter provided for a conventional energy analyzer of a spherical mirror-spherical grid retarding potential type, as disclosed in U.S. Pat. No. 3,749,926 granted to Jerald D. Lee, issued on July 31, 1973, entitled "Charged Particle Energy Analysis".

The geometry of FIG. 1 contains a low energy pass reflection filter and a high energy pass transmission filter. The low energy pass reflection filter is featured by selectively reflecting charged particles having energy lower than a predetermined value. The high energy pass transmission filter is featured by selectively transmitting electrons having energy higher than a predetermined value.

In FIG. 1, the low energy pass filter is provided with a spherical mirror M having a curvature center O, and a spherical grid $G_1$, which are arranged concentrically. The high energy pass transmission filter is provided with double spherical grids $G_2$ and $G_3$ having the curvature center O. The mirror M has a potential of $V_1$. The grid $G_3$ has another potential of $V_2$. The grids $G_1$ and $G_2$ are placed in the same potential of $V_a$ and appropriate voltage are applied between the grid $G_1$ and the spherical mirror M, and the grids $G_2$ and $G_3$.

When an injection point from which charged particles are diverged is disposed at a point S adjacent the center O, the charged particles having energy lower than $e|V_1|$ are reflected by the mirror M, so that they are converged to a point adjacent the center O. They are diverged toward the high energy pass transmission filter. The charged particles having energy higher than $e|V_2|$ are transmitted through the grid $G_3$.

Finally, the charged particles having energy higher than $e|V_2|$ and lower than $e|V_1|$ can be collected by a detector disposed behind the grid $G_3$. The charged particles diverged from the point S have energy of subtracting a potential applied to another grid from the energy of charged particles emitted from a sample, using a retarding field. By selecting the potential of this grid, the charged particles having a selected energy band width can be obtained.

However, since the low energy pass reflection filter and the high energy pass transmission filter must be disposed on opposite sides of the curvature center O, the energy analyzer must be large. Furthermore, a sample cannot be placed close to the point S because there is no space to set an exciting source such as an X-ray source or an electron gun, near the sample, so the apparatus therefore needs a complicated lens system to focus the charged particles from the excited sample surface to the point S.

Usually, the lens system reduces the transmission of the charged particles according to the particle energy.

Therefore, it is desired to provide a compact charged particle energy analyzer, which has no lens system.

SUMMARY OF THE INVENTION

Accordingly, it is an object of the present invention to provide an improved charged particle energy analyzer of high sensitivity.

It is another object of the present invention to provide a compact, lensless and high luminosity charged particle energy analyzer comprising the energy analyzing elements disposed on one side of a curvature center of a reflective mirror.

It is a further object of the present invention to provide an improved arrangement of a charged particle energy analyzer in which a detector can be disposed at a focus position.

It is a further object of the present invention to provide an improved arrangement of a charged particle energy analyzer in which an exciting source element such as an X-ray gun, an electron gun or an ion gun is positioned at one side of the analyzer.

It is a further object of the present invention to provide an improved charged particle energy analyzer in which a spheroid mirror is provided for reflecting charged particles.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a charged particle energy analyzer comprises a source or a gun for generating radiation to be incident on a sample so as to emit charged particles from the sample, a low energy pass reflection filter means for selectively reflecting the charged particles having energy lower than a first value, the low energy pass reflection filter means comprising a reflector and a first grid means, and a high energy pass transmission filter means for selectively transmitting the charged particles having energy higher than a second value.

The reflector has two complex focuses, in symmetric relation, at which the sample and a detector means are disposed. The detector detects the charged particles selected.

The charged particle energy analyzer is adapted for electron spectroscopy for chemical analysis (ESCA), XPS, AES, and SIMS.

BRIEF DESCRIPTION OF THE DRAWINGS

The present invention will become more fully understood from the detailed description given hereinbelow and the accompanying drawings which are given by way of illustration only, and thus are not limitative of the present invention and wherein:

FIG. 1 shows one of the conventional combinations of a low energy pass reflection filter and a high energy pass transmission filter for a conventional charged particles energy analyzer;

FIG. 2 shows a construction of a charged particle energy analyzer according to the present invention;

FIG. 3 shows a graph representing characteristics of a filter means provided in the analyzer as shown in FIG. 2; and FIG. 4 shows an enlarged view of a filter means for reflecting charged particles according to the present invention.

DESCRIPTION OF THE PREFERRED EMBODIMENT

FIG. 2 shows a construction of a charged particle energy analyzer applied for electron spectroscopy for chemical analysis (ESCA) according to the present invention. It may be evident that the charged particle energy analyzer of FIG. 2 is adapted for XPS, AES, and SIMS.

The charged particle energy analyzer of FIG. 2 comprises an analyzer body 1, and inlet sleeve 2, an outlet sleeve 3, a first grid $G_1$, a second grid $G_2$, a third grid $G_3$, a fourth grid $G_4$, a fifth grid $G_5$, and a sixth grid $G_6$, a spheroid mirror 4, electrostatic shields 5, exhaustion ports 6, and an electron multiplier 7.

The above-constructed analyzer is shielded by a magnetic shield 20. An X-ray gun 8 with an X-ray filter 9 is provided adjacent the analyzer. A sample 10 is disposed under the inlet sleeve 2, being adjacent the X-ray gun 8. The analyzer, the X-ray gun 8, and the sample 10 are disposed within a vacuum chamber 11 for vacuum pumping.

The X-ray gun 8 is provided for irradiating the sample 10 with a beam of characteristic X-rays, so that the charged particles, are emitted from the sample 10. It may be possible that the X-ray gun 8 is replaced by an electron gun or an ion gun. The charged particles disperse toward the inlet sleeve 2. The outlet sleeve 3 receives the photoelectrons selected in accordance with the principle of the present invention by the grids.

The spheroid mirror 4 has two focuses, one close to the central surface of the sample 10 and another close to the central surface of the electron multiplier 7, which are symmetrical about the central axis of the mirror 4. The analyzer body 1 covers the analyzer completely. The third grid $G_3$ is disposed in front of the spheroid mirror 4, so that the grid $G_3$ is parallel with the mirror 4. The third grid $G_3$ and the spheroid mirror 4 form a low energy pass reflection filter. The first grid $G_1$ is provided for preventing performance decrease from static sample charging. The second grid $G_2$ is provided for making a retarding field. The first grid $G_1$ and the second grid $G_2$ are arranged at the inlet sleeve 2. These grids $G_1$ and $G_2$ are concentric with the center of the sample 10.

The fourth grid $G_4$, the fifth grid $G_5$ and the sixth grid $G_6$ are disposed at the outlet sleeve 3. The photoelectrons having high energy can pass through the fifth grid $G_5$. The sixth grid $G_6$ is provided to accelerate the photoelectrons. The fourth grid $G_4$, the fifth grid $G_5$ and the sixth grid $G_6$ are concentric with the center of the electron multiplier 7.

The ring 12 is provided for supporting the third grid $G_3$. The mirror 4 may be made from aluminum and has a spheroidal reflection surface. On the surface of the mirror 4, carbon 14 is coated to give the surface better conductivity and to reduce emission of secondary electrons. The insulators 13 are made from ceramic whose surface is coated with film having high resistivity and serve as guard rings for preventing field disturbance at the ends between the spheroid mirror 4 and the third grid $G_3$, the first grid $G_1$ and the second grid $G_2$, and the fourth grid $G_4$ and the fifth grid $G_5$, respectively.

The exhaustion ports 6 are provided through which air can be easily evacuated from the analyzer body 1.

The electrostatic shield 5 is provided to prevent the field effect through the ports from the outer part. The electron multiplier 7 is provided for detecting the photoelectrons to measure the energy of them.

While the photoelectrons are emitted from the sample 10 in response to the irradiation of the characteristic X-rays by the X-ray gun 8, the irradiated photoelectrons are received by the inlet sleeve 2. At this time, the respective parts have the following voltage.

The sample 10: 0 volt
The first grid $G_1$: 0 volt
The second grid $G_2$: $-V_A$ volt
The third grid $G_3$: $-V_A$ volt
The spheroid mirror 4: $-V_A - (E_0' + \Delta E'/2)$ volt $(=V_1)$
The fourth grid $G_4$: $-VA$ volt
The fifth grid $G_5$: $-VA - (E_0 - \Delta E/2)$ volt $(=V_2)$
The sixth grid $G_6$: $[-VA - (E_0 - \Delta E/2) + V_D]$ volt
where $\Delta E$ = a half width volt, $V_D$ = 100–200 volt preferably
$V_A$ = 0–3000 volt
$eEo$(analyzer pass energy) = 0–200 eV.
$eE_o' = eE_o \cdot \cos\theta$, $\Delta E' = \Delta E \cdot \cos\theta$ The sample 10 and the first grid $G_1$ are both grounded together with the inlet sleeve 2 at the interval between the sample 10 and the first grid $G_1$. As stated above, the second grid $G_2$ is provided for reflecting the photoelectrons having the energy lower than $eV_A$. The first and second grids $G_1$ and $G_2$ form a high energy pass transmission filter. The photoelectrons having the energy higher than $eV_A$ can pass through the second grid $G_2$. The second grid $G_2$, the third grid $G_3$ and the fourth grid $G_4$ are all biased with the same voltage together with the analyzer body 1 surrounding these grids $G_2$, $G_3$ and $G_4$. Therefore, around the space surrounded by these grids $G_2$, $G_3$ and $G_4$, and the analyzer body 1, the same voltage is applied. The voltage $V_A$ is to scan the energy.

The photoelectrons passing through the second grid $G_2$ go towards the third grid $G_3$ after passing through the abovestated space. The spheroid mirror 4 is provided for selectively reflecting the photoelectrons. The third grid $G_3$ and the spheroid mirror 4 form a low energy pass reflection 5 filter. Since the absolute value of the voltage at the spheroid mirror 4 is more than that of the voltage at the third grid $G_3$, namely, $-(V_A + E_o' + \Delta E'/2)$ volt, the photoelectrons having the energy smaller than $e(V_A + E_o + \Delta E/2)$ are reflected by the mirror 4 and the photoelectrons having the energy larger than $e(V_A + E_o + \Delta E/2)$ collide with the mirror 4 to thereby consume the energy. The analyzer pass energy $E_o$ is referred to pass energy of the photoelectrons in the analyzer.

Since the spheroid mirror 4 has two focuses, one close to the center of the sample 10 and the other close to the center of the electron multiplier 7, the photoelectrons reflected by the spheroid mirror 4 are directed straight toward the center of the outlet sleeve 3. The photoelectrons reflected by the spheroid mirror 4 can pass through the fourth grid $G_4$ having the voltage of $-V_A$. The fourth and fifth grids $G_4$ and $G_5$ are provided for selectively transmitting the photoelectrons as another high energy pass transmission filter. Therefore, the photoelectrons having the energy smaller than $e(-V_A + E_o - \Delta E/2)$ are reflected by the fifth grid $G_5$ and the photoelectrons having the energy larger than $e(-V_A + E_o - \Delta E/2)$ pass the fifth grid $G_5$. The sixth grid $G_6$ with applied voltage $V_D$ is provided for accelerating the photoelectrons.

Thus, the photoelectrons are converged at the electron multiplier 7, the electrons having the energy larger than $e(V_A+E_o-\Delta E/2)$ as selected by the fifth grid $G_5$ and smaller than $e(V_A+E_o+\Delta E/2)$ as selected by the spheroid mirror 4. Thus, the electron multiplier detects the electrons having the band energy $e \cdot \Delta E$.

FIG. 3 shows a graph representing the voltages applied to the grids and the spheroid mirror 4 and the filter characteristic according to the present invention. With the help of the low energy pass reflection filter provided by the third grid $G_3$ and the spheroid mirror 4 and the high energy pass transmission filter provided by the fourth and fifth grids $G_4$ and $G_5$, the photoelectrons having the energy in a half width of $e \cdot \Delta E$ can be selected which are detected by the electron multiplier 7.

In FIG. 3, $F_1$ represents transmittance of energy in the high energy transmission filter formed by the first and second grids $G_1$ and $G_2$. $F_2$ represents transmittance of energy in the low energy pass reflection filter formed by the third grid $G_3$ and the spheroid mirror 4. $F_3$ represents transmittance of energy in the high energy transmission filter formed by the fourth and fifth grids $G_4$ and $G_5$. $\Delta E$ represents a half width volt meaning full width at half maximum (FWHM) of transmittance of the analyzer.

In accordance with the above principle, the energy analysis are carried out by changing the value of $V_A$ to be applied to the second, third, and fourth grids $G_2$, $G_3$ and $G_4$, the voltages of the second, third, and fourth grids $G_2$, $G_3$ and $G_4$ being made identical, and the voltage difference between these grids and the spheroid mirror 4, on the one hand and the fifth grid $G_5$ on the other hand is constant.

On the position of the electron multiplier 7, the electron image of the sample 10 is made. The photoelectrons passed through the fifth grid $G_5$ are so slow, as to be zero electron volt. The sixth grid $G_6$ is provided for accelerating the photoelectron pass through the fifth grid $G_5$.

To observe the sample image of the photoelectrons selected in accordance with the above filtering operation, the sixth grid $G_6$ is needed between the fifth grid $G_5$ and the electron multiplier 7 for keeping the electron beam from grid $G_5$ from going straight to the detector and obtaining the good image, because the orbit of the electrons having very low energy are easily disturbed by the outer undesired electrostatic potential and magnetic field. In order to obtain information of the image usually a position sensitive means such as a channel plate or a fluorescent screen followed by a video camera is positioned instead of the detector.

In the above preferred embodiment, the reflector is a spheroid mirror. However, it may be possible that a spherical mirror replaces the spheroid mirror 4 when the distance between the sample 10 and the multiplier 7 is small as compared with the distances between the mirror surface and the sample 10 and the multiplier 7.

Such a spherical mirror is disposed at a central point between the optical distance between the sample 10 and the multiplier 7. FIG. 4 shows an enlarged view of a filter means such as the third grid $G_3$ and the spheroid mirror 4. It is now described that strictly speaking, the principal ray in the analyzer in FIG. 2 is reflected by the spheroid mirror 4 as shown in FIG. 4. Before the photoelectrons pass through the third grid $G_3$, they run straight. After the photoelectrons pass through the third grid $G_3$, they run showing a parabola trace to thereby be reflected by the spheroid mirror 4 and be emitted out of the third grid $G_3$.

When the distance between the spheroid mirror 4 and the third grid $G_3$ is d, an apparent reflection face is a spheroid face separated at the distance d from the spheroid mirror 4. Therefore, the focuses of the center of the spheroid mirror 4 and the detector 7 are not the focus of the spheroid mirror 4, but one of a spheroid face 4'.

As stated above, in accordance with the present invention, the spheroid mirror is provided which has two complex focuses. On the two complex focuses, the sample and the electron multiplier are disposed. Therefore, the photoelectrons irradiated from the sample are introduced directly into the analyzer. In addition, the sample, the X-ray gun, and the electron multiplier are disposed outside the analyzer, so that the photoelectrons in the analyzer are not prevented from raying. The photoelectrons irradiated from the sample with wide solid angles are not lost.

Therefore, the system of the present invention provides high sensitivity concerning the photoelectrons as compared with the system of FIG. 1. Since the energy analyzing elements are gathered at one side of the curved surface of the reflected mirror, the size of the system of FIG. 2 can be half of that of system of FIG. 1.

The advantages of the present invention are summarized as follows:

1. No lens system for focusing the charged particles emitted from the sample is required. The gun and other elements are positioned on only one side of the analyzer. The mirror having a spheroidal reflection surface is used. Therefore, high sensitivity of the analyzer is attained with a compact system.

2. The detector is positioned at the image point of the sample. Therefore, the position sensitive analysis can be performed.

3. Totally, the analyzer is highly sensitive and superior.

The invention being thus described, it will be obvious that the same may be varied in many ways. Such spirit and scope of the invention, and all such modifications are intended to be included within the scope of the following claims.

What is claimed is:

1. A charged particle energy analyzer comprising:
    source means for generating radiation and directing said radiation to be incident on a sample so as to emit charged particles from the sample;
    low energy pass reflection filter means for selectively reflecting charged particles having energy lower than a first value, said low energy pass reflection filter means comprising a reflector and first grid means,
    high energy pass transmission filter means for selectively transmitting charged particles having energy higher than a second value; and
    detector means for detecting said charged particles;
    wherein said reflector of said low energy pass reflection filter means has two complex focuses symmetrically disposed with respect to the center of said reflector; and
    said sample is positioned at one of said focuses and said detector is positioned at the other of said focuses.

2. The analyzer according to claim 1, wherein said reflector is a spheroid reflector.

3. The analyzer according to claim 1, wherein said detector is a position-sensitive detector for obtaining information regarding the image of the sample.

4. The analyzer according to claim 1, further comprising an additional grid disposed between said high energy pass transmission filter means and said detector for accelerating the charged particles.

5. The analyzer according to claim 1, wherein both said high and low energy pass filter means are contained within a space generally between said reflector and a surface containing said two focuses of the reflector.

6. The analyzer according to claim 5, wherein said high energy pass transmission filter means comprises first filter means and second filter means, said first filter means being disposed in front of the sample and said second filter means being disposed in front of said detector.

7. A charged particle energy analyzer comprising:
source means for generating radiation and directing said radiation to be incident on a sample so as to emit charged particles from the sample;
low energy pass reflection filter means for selectively reflecting charged particles having energy lower than a first value, said low energy pass reflection filter means comprising a reflector and grid means;
high energy pass transmission filter means for selectively transmitting charged particles having energy higher than a second value; and
detector means for detecting the charged particles;
wherein said reflector has a center of curvature and said sample and said detector are positioned symmetrically with respect to a line connecting said center of curvature with a point on said reflector; and
said high energy pass transmission filter is positioned within a space generally between the reflector on the one hand and the sample and detector on the other hand.

8. The analyzer according to claim 7, wherein said reflector is a spherical reflector.

9. A charged particle energy analyzer comprising:
source means for directing radiation to be incident on a sample so as to emit charged particles from the sample;
low energy pass filter means for selectively passing charged particles having energy lower than first value;
reflector means for reflecting said charged particles;
high energy pass filter means for selectively passing charged particles having energy higher than a second value; and
detector means for detecting said charged particles;
wherein said reflector means has two complex focuses symmetrically disposed with respect to the center of said reflector; and
said sample is positioned at one of said focuses and said detector is positioned at the other of said focuses; and
wherein both said high and low energy pass filter means are contained within a space generally between said reflector and a surface containing said two focuses of the reflector.

* * * * *